US009474822B2

(12) United States Patent
Jung et al.

(10) Patent No.: US 9,474,822 B2
(45) Date of Patent: Oct. 25, 2016

(54) STERILIZATION AND DEODORIZATION APPARATUS

(71) Applicant: LG ELECTRONICS INC., Seoul (KR)

(72) Inventors: Yeekyeong Jung, Seoul (KR); Kyungsoo Yoon, Seoul (KR); Jaesoo Jang, Seoul (KR); Bongjo Sung, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 14/799,941

(22) Filed: Jul. 15, 2015

(65) Prior Publication Data

US 2016/0015848 A1   Jan. 21, 2016

(30) Foreign Application Priority Data

Jul. 16, 2014   (KR) .................... 10-2014-0089497

(51) Int. Cl.
*A61L 9/22* (2006.01)
*A61L 9/12* (2006.01)

(52) U.S. Cl.
CPC .. *A61L 9/12* (2013.01); *A61L 9/22* (2013.01); *A61L 2209/12* (2013.01); *A61L 2209/14* (2013.01); *A61L 2209/212* (2013.01)

(58) Field of Classification Search
CPC ....................................................... A61L 9/12
USPC ....................................................... 422/121
See application file for complete search history.

(56) References Cited

U.S. PATENT DOCUMENTS

| 7,674,436 B1* | 3/2010 | Feldman ............... A61L 9/205 250/432 R |
| 2006/0056129 A1 | 3/2006 | Kim et al. |
| 2008/0170971 A1 | 7/2008 | Bergeron et al. |
| 2009/0010801 A1* | 1/2009 | Murphy ............ B01D 46/0028 422/4 |
| 2009/0207548 A1 | 8/2009 | Seto et al. |
| 2009/0223806 A1 | 9/2009 | Thevenet et al. |
| 2011/0216467 A1* | 9/2011 | Itani ..................... B03C 3/09 361/231 |

(Continued)

FOREIGN PATENT DOCUMENTS

| EP | 1 980 317 | 10/2008 |
| EP | 1 547 693 | 6/2015 |

(Continued)

OTHER PUBLICATIONS

English Translation of Document No. JP 2000246116 A provided by www.j-platpat.inpit.go.jp: Gas liquid purifying cylinder composed of photocatalyst imparted rotary structural body, Dec. 9, 2000.*

(Continued)

*Primary Examiner* — Kevin Joyner
*Assistant Examiner* — Holly Mull
(74) *Attorney, Agent, or Firm* — KED & Associates LLP

(57) ABSTRACT

A sterilization and deodorization apparatus is provided. The sterilization and deodorization apparatus may include a frame that defines an outer appearance of the sterilization and deodorization apparatus, a plasma unit or device disposed on or at one or a first side of the frame, the plasma unit forming a plasma region to generate a plurality of ions, and a filter unit or filter disposed on the other or a second side of the frame which is spaced apart from the frame. The filter unit may include a filter frame having a plurality of throughholes so that air passes therethrough, and a photocatalyst applied to the filter frame to perform photocatalytic reaction.

20 Claims, 15 Drawing Sheets

(56) References Cited

U.S. PATENT DOCUMENTS

2013/0119264 A1    5/2013   Yagi et al.
2015/0125356 A1*   5/2015   Miyamoto ................ A61L 9/22
                                                              422/186.07

FOREIGN PATENT DOCUMENTS

| EP | 2 923 752 | 9/2015 |
| JP | 2000246116 A * | 9/2000 |
| JP | 2013-258137 | 12/2013 |
| KR | 10-2006-0024845 | 3/2006 |
| KR | 10-0657476 | 12/2006 |
| WO | WO 2007/070704 | 6/2007 |

OTHER PUBLICATIONS

European Search Report dated Nov. 12, 2015.
U.S. Appl. No. 14/660,126, filed Mar. 17, 2015.
U.S. Appl. No. 14/799,885, filed Jul. 15, 2015.
European Search Report dated Dec. 3, 2015.

* cited by examiner

STERILIZATION AND DEODORIZATION APPARATUS

CROSS-REFERENCE TO RELATED APPLICATION(S)

The present application claims priority under 35 U.S.C. 119 and 35 U.S.C. 365 to Korean Patent Application No. 10-2014-0089497, filed in Korea on Jul. 16, 2014, which is hereby incorporated by reference in its entirety.

BACKGROUND

1. Field

A sterilization and deodorization apparatus is disclosed herein.

2. Background

In recent years, introduction of external gas into buildings may be minimized to reduce energy consumption. Accordingly, due to air-tight buildings, indoor air pollution in the buildings is becoming more serious. As a result, various kinds of judiciary regulations with respect to indoor pollutants are being increasingly enforced.

While home appliances installed in homes or companies operate, indoor pollutants may be generated and deposited within the home appliances or discharged from the home appliances. The indoor pollutants may cause an unpleasant smell and have a bad impact on a user's health.

For example, in a case of home appliances using air containing moisture or water, such as air conditioners, dehumidifiers, air cleaners, refrigerators, or washing machines, pollution due to dust or microorganisms inside or outside the home appliances may occur. In detail, the Indoor pollutants may be classified into (1) particle pollutants, such as fine dust, and asbestos, for example, (2) gas pollutants, such as voltaic organic compounds (VOCs), and (3) biological pollutants, such as viruses, and molds, for example.

To remove the indoor pollutants, surface discharge induced plasma chemical processing may be used. In general, the surface discharge induced plasma chemical processing may be understood as or refer to a process in which a strong plasma region is formed on a surface of a device through high frequency discharging using ceramic to generate a large amount of OH radicals and ozone, thereby removing the pollutants using the generated radicals and ozone.

The present Applicant has filed an application (hereinafter, referred to as a "related art") with respect to the above-described technology, Korean Patent Registration No. 10-0657476, entitled "Surface Discharge Induced Air Purifier" and registered on Dec. 7, 2006, which is hereby incorporated by reference. The air purifier according to the related art includes a plasma electrode device including a discharge electrode disposed on a top surface of two sheets of insulating dielectrics, which are attached to each other, a ground electrode disposed between the two sheets of insulating dielectrics, and a coating layer that shields the discharge electrode to prevent the discharge electrode from being directly exposed to air.

However, in the air purifier according to the related art, as ozone is generated as a result of the reaction, it may be necessary to satisfy mandatory controls with respect to the ozone, and also, pernicious influences on the human body may occur due to the ozone.

BRIEF DESCRIPTION OF THE DRAWINGS

Embodiments will be described in detail with reference to the following drawings in which like reference numerals refer to like elements, and wherein.

DETAILED DESCRIPTION

Figure 1:
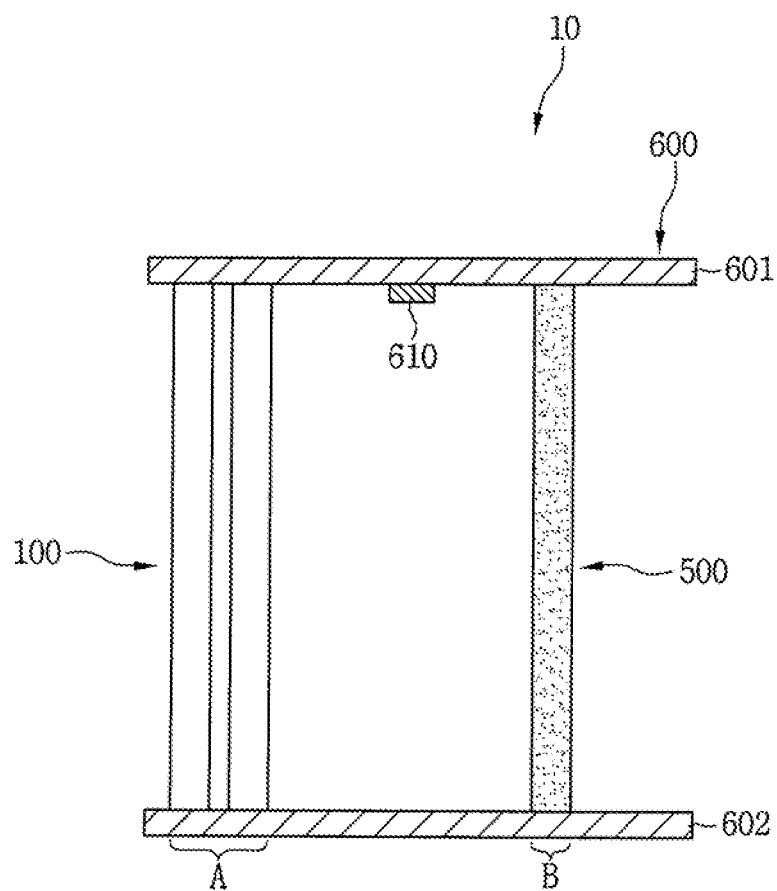
FIG. 1 is a cross-sectional view of a sterilization and deodorization apparatus according to embodiment.

FIG. 1 is a cross-sectional view of a sterilization and deodorization apparatus according to an embodiment. Referring to FIG. 1, a sterilization and deodorization apparatus 10 according to an embodiment may include a plasma unit or device 100 that forms a plasma region to generate OH radicals and ozone, a filter unit or filter 500 disposed to be spaced apart from the plasma unit 100 and having a plurality of through-holes, and a frame 600 that surrounds upper and lower ends of the plasma unit 100 and the filter unit 500 to support the plasma unit 100 and the filter unit 500.

The frame 600 may include a first frame 601 disposed on the upper ends of the plasma unit 100 and the filter unit 500, and a second frame 602 disposed on the lower ends of the plasma unit 100 and the filter unit 500. The plasma unit 100 and the filter unit 500 may be supported within the frame 600 by the first and second frames 601 and 602.

A light source 610 that irradiates light may be disposed on a bottom surface of the first frame 601. The light source 610 may be disposed on the bottom surface of the first frame 601 between the plasma unit 100 and the filter unit 500. A photocatalyst provided in the filter unit 500 may be activated by the light emitted from the light source 610. For example, the light emitted from the light source 610 may have a wavelength of or in a visible light region.

Figure 2:
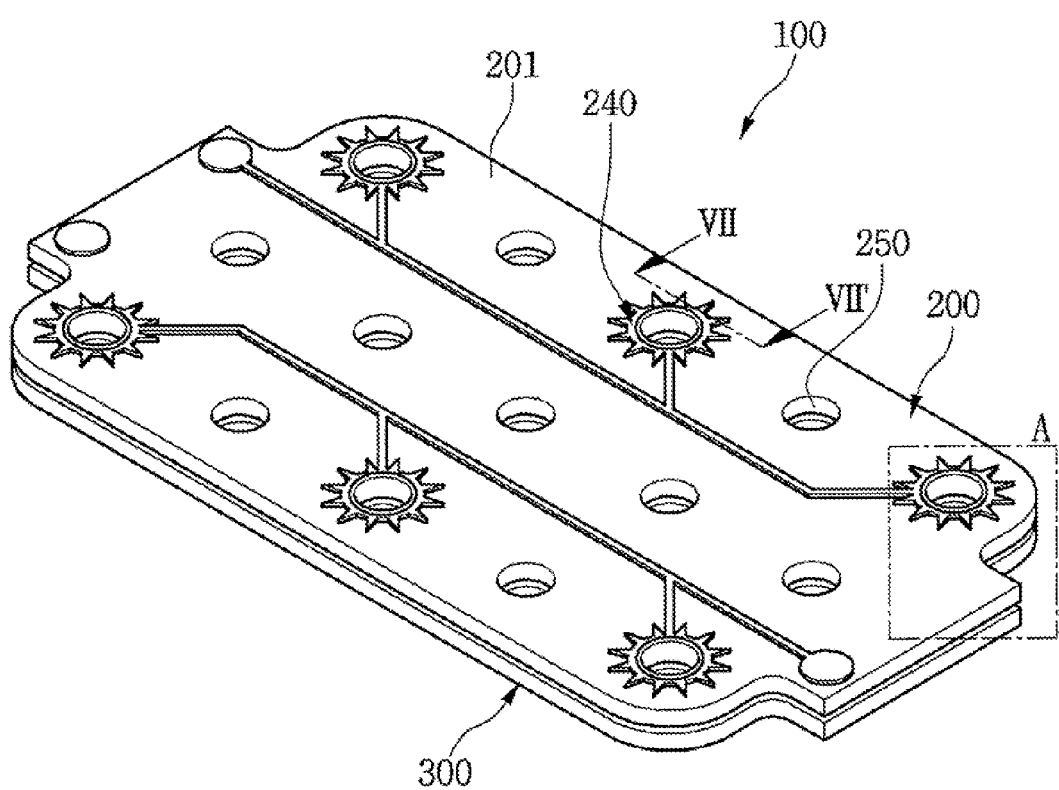
FIG. 2 is a perspective view of a plasma unit or device according to an embodiment.
Figure 3:
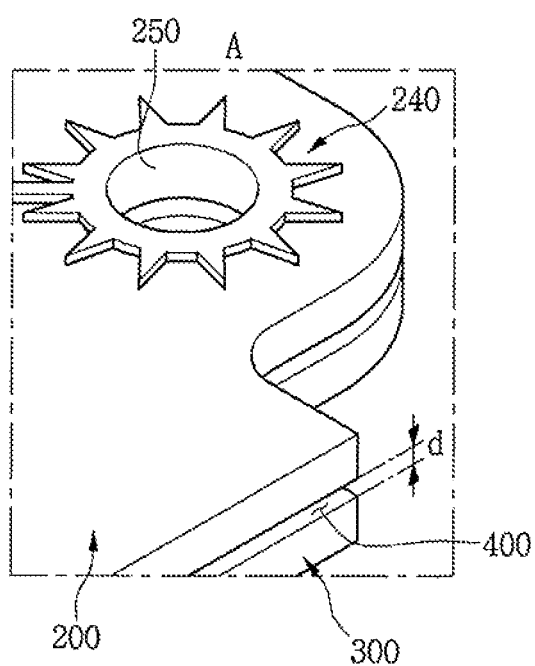
FIG. 3 is an enlarged view illustrating a portion A of FIG. 2.
Figure 4:
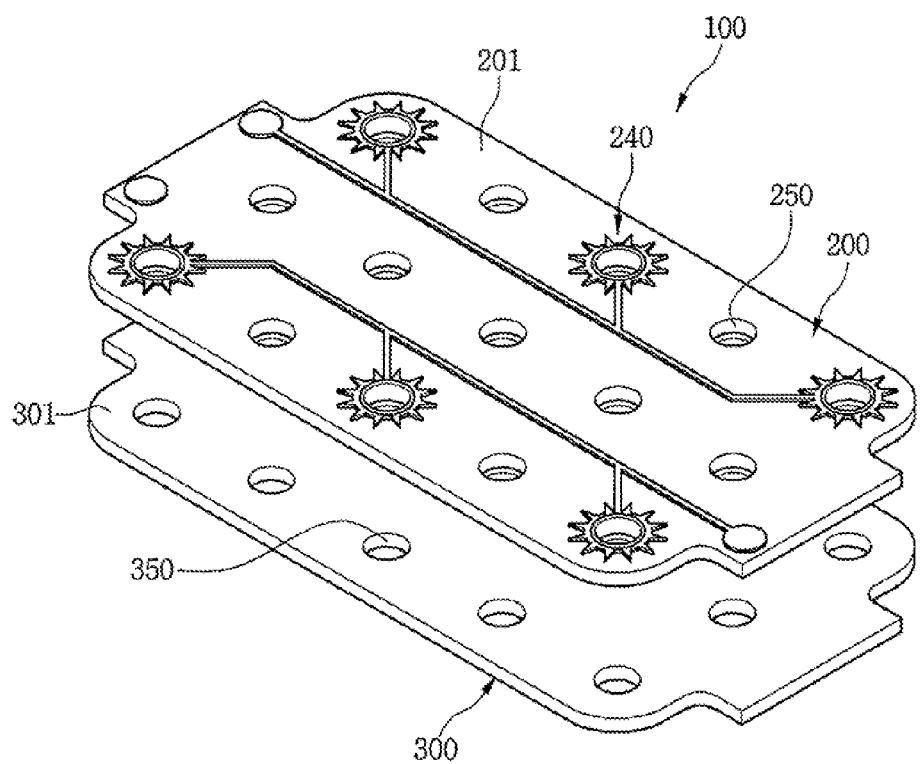
FIG. 4 is an exploded perspective view of the plasma unit of FIG. 2.

Hereinafter, the plasma unit 100 will be described, and then, the fitter unit 500 will be described. FIG. 2 is a perspective view of a plasma unit or device according to an embodiment. FIG. 3 is an enlarged view illustrating a portion A of FIG. 2. FIG. 4 is an exploded perspective view of the plasma unit of FIG. 2.

Referring to FIGS. 2 to 4, the plasma unit or device 100 according to this embodiment may include first and second substrates 200 and 300, which may be disposed opposite to each other. For example, the second substrate 300 may be disposed below the first substrate 200, and the first and second substrates 200 and 300 may have a same size and shape. The first substrate 200 may be called an "upper plate", and the second substrate 300 may be called a "lower plate".

In detail, a distance formation part or portion 400 by which the first and second substrates 200 and 300 are spaced by a set or predetermined distance d from each other may be provided between the first and second substrates 200 and 300. For example, the set distance d may have a value of several micrometers (μm).

The first substrate 200 may include a first substrate body 201 having an approximately rectangular shape, and at least one first flow hole 250 that passes through the first substrate body 201 to guide a flow of air. For example, a plurality of the first flow hole 250 may be provided. That is, as illustrated in FIG. 4, 15 first flow holes 250 may be provided; however, embodiments are not limited to a number of flow holes.

The first substrate 200 may include a first discharge electrode 240 including a pattern frame (see reference numeral 243 of FIG. 5) disposed to surround at least one first flow hole 250 of the plurality of first flow holes 250. For example, the pattern frame 243 may surround 6 first flow holes 250 of the 15 first flow holes 250; however, embodiments are not limited thereto.

The second substrate 300 may include a second substrate body 301 having an approximately rectangular shape, and at least one second flow hole 350 that passes through the second substrate body 301 to guide a flow of air. For example, a plurality of the second flow hole 350 may be provided. That is, as illustrated in FIG. 5, 15 second flow holes 350 may be provided, like the first flow holes 250; however, embodiments are not limited to a number of flow holes.

The plurality of second flow holes 350 may communicate with the plurality of first flow holes 250, respectively. The plurality of second flow holes 350 may be defined below the plurality of first flow holes 250. While the plasma unit 100 operates to perform plasma discharge, air passing through the plurality of first and second flow holes 250 and 350 may be oxidized or decomposed.

Figure 5:
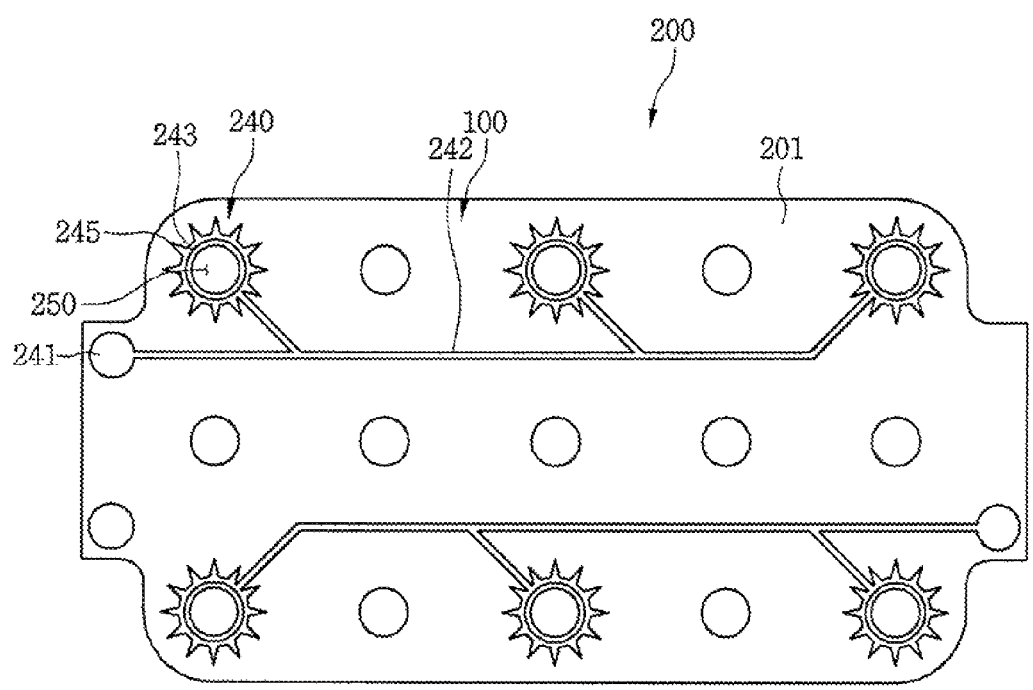
FIG. 5 is a plan view of a first substrate according to an embodiment.
Figure 6:
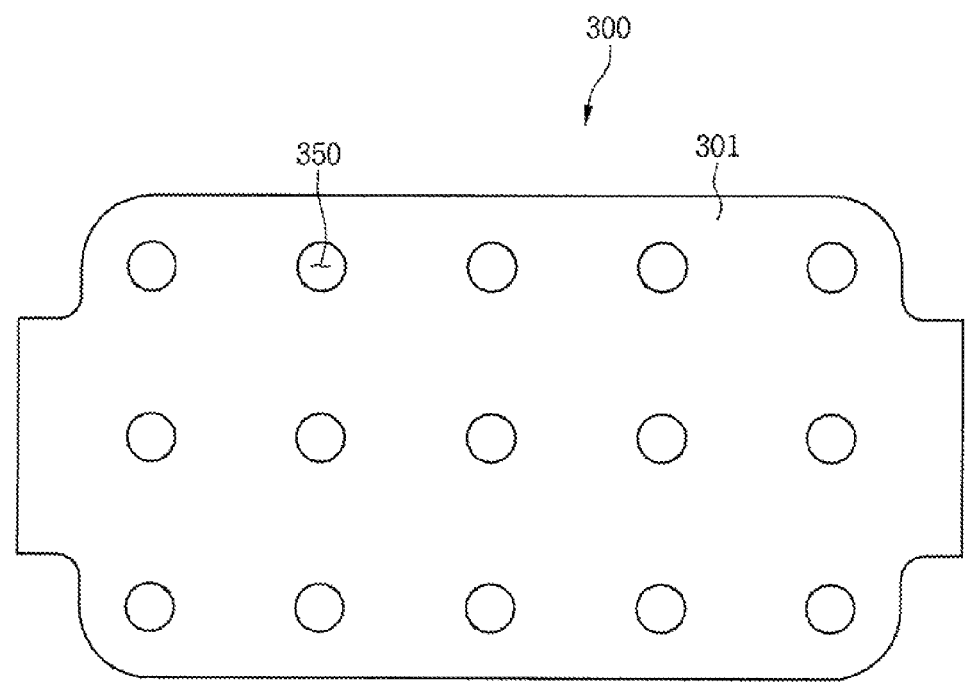
FIG. 6 is a plan view of a second substrate according to an embodiment.
Figure 7:
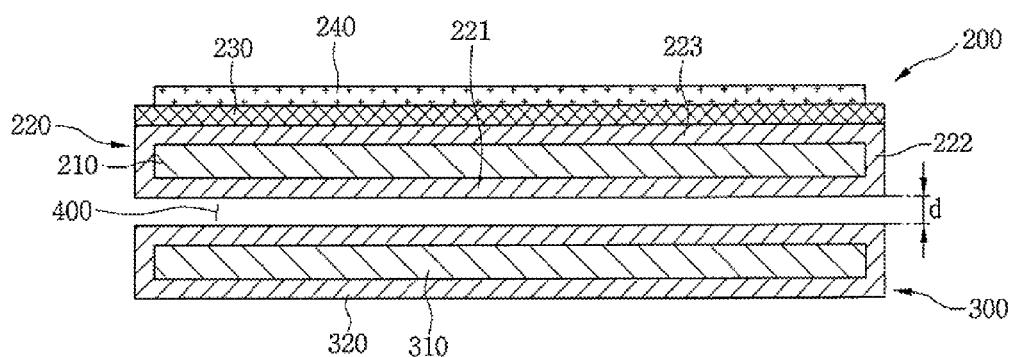
FIG. 7 is a cross-sectional view taken along line VII-VII' of FIG. 2.

FIG. 5 is a plan view of a first substrate according to an embodiment. FIG. 6 is a plan view of a second substrate according to an embodiment. FIG. 7 is a cross-sectional view taken along line VII-VII' of FIG. 2.

Referring to FIG. 5, the first substrate 200 according to an embodiment may include the first substrate body 201 having a plurality of the first flow holes 250, and the first discharge electrode 240 disposed on one surface of the first substrate body 201. The first substrate body 201 may include a ground electrode 210, a first insulator 220 that surrounds the ground electrode 210, and a photocatalyst part 230 disposed on at least one surface of the first insulator 220. The first substrate body 201 will be described in detail hereinbelow.

The first discharge electrode 240 may include a discharge electrode part or portion 241 to which power may applied, the pattern frame 243, which may be disposed to surround at least a portion of the first flow holes 250, and at least one discharge tip 245 disposed on the pattern frame 243. A plurality of the pattern frame 243 may be provided. Each pattern frame 243 may include a closed pattern that surrounds the respective first flow hole 250. Further, each pattern frame 243 may have a circular shape, an oval shape, or a polygonal shape, for example. The at least one discharge tip 245 may protrude from an outer circumferential surface of the pattern frame 243.

The first discharge electrode 240 may further include a connection line 242 that extends from the discharge electrode part 241 toward the plurality of pattern frames 243. The connection line 242 may be branched from the plurality of pattern frames 243.

The first discharge electrode 240 may be formed by printing metal oxide paste, for example. A metal material of the metal oxide paste may be selected from the group consisting of tungsten, iron, copper, platinum, and silver, for example. For example, the metal material may be silver (Ag).

Silver oxide paste may be printed on the first discharge electrode 240. As the silver oxide paste has a resistance of about 10Ω to about 20Ω, discharge may be easily performed due to low resistance. Thus, the discharge may be uniformly generated over the electrode. Also, the silver oxide paste may reduce an amount of ozone through the discharge.

Referring to FIG. 6, the second substrate 300 according to an embodiment may include the second substrate body 301 having a plurality of the second flow holes 350. The second substrate body 301 may include a second discharge electrode 310, and a second insulator 320 that surrounds the second discharge electrode 310. The second substrate body 301 will be described hereinbelow with reference to FIG. 7.

Referring to FIG. 7, the first substrate body 201 of the first substrate 200 according to this embodiment may include the ground electrode 210 that interacts with the first discharge electrode 240 or the second discharge electrode 310 to perform the plasma discharge, and the first insulator 220 that surrounds the ground electrode 210 to prevent the ground electrode 210 from being exposed to the outside. The ground electrode 210 may be formed of a metal plate, for example, copper (Cu), and the first insulator 220 may be formed of an epoxy resin, for example.

The first insulator 220 may include a bottom surface part or bottom surface 221, on which the ground electrode 221 may be seated, a side surface part or side surface 222 that extends upward from each of both sides of the bottom surface part 221, and a top surface part or top surface 223 coupled to an upper portion of the side surface part 222. An outside of the ground electrode 210 may be completely surrounded by the bottom surface part 221, the side surface part 222, and the top surface part 223 of the first insulator 210.

A method of manufacturing the ground electrode 210 and the first insulator 220 will be described hereinafter. The ground electrode 210 may be printed (masked) on an upper portion of the bottom surface part 221 of the first insulator 220. The bottom surface part 221 may be formed of an epoxy resin, for example, and may be understood as or refer to a "base" on which the ground electrode 210 may be disposed.

When the ground electrode 210 is printed, a bottom surface of the ground electrode 210 may be covered by the first insulator 220, and side and top surfaces of the ground electrode 210 may be exposed to the outside. The side surface part 222 and the top surface part 223 of the first insulator 220 may be applied to the side and top surfaces of the ground electrode 210, which may be exposed to the outside. The applied side surface part 222 and top surface part 223 may be formed of the same epoxy resin as the bottom surface part 221.

The photocatalyst part 230, which may react or be activated by visible light, may be disposed on the first insulator 220. That is, the photocatalyst part 230 may be disposed between the first insulator 220 and the first discharge electrode 240. The photocatalyst part 230 may decompose various harmful substances, perform antibacterial and sterilization functions, and reduce an amount of ozone, for example.

The visible light may be understood as or refer to external light existing outside of the plasma unit 100. For example, the visible light may include natural light or a lighting source that exists in a predetermined space.

The photocatalyst part 230 may include a plurality of compositions. In detail, the plurality of composites may include silver phosphate (AgsPO$_4$), titanium dioxide (TiO$_2$), and an inorganic binder, for example. For example, the plurality of composites may include about 20 to about 50 parts by weight of silver phosphate (Ag$_3$PO$_4$), about 5 to about 40 parts by weight of titanium dioxide (TiO$_2$), and about 10 to about 40 parts by weight of the inorganic binder.

Titanium dioxide (TiO$_2$) may have high activity when UV rays are irradiated and be chemically stable without being eroded by an acid, a base, and an organic solvent. Silver phosphate (Ag$_3$PO$_4$) may cause a catalytic activity reaction by optical energy having a visible-ray wavelength range of about 385 nm or more and a mean wavelength of about 500 nm. As the silver phosphate is mixed with the titanium dioxide, the photocatalyst part 230 may be effectively activated by the visible light.

The silver phosphate (AgsPO$_4$) in itself may have antibacterial (bacteria and mold, for example) performance, and a synergy effect, such as decomposition efficiency of organic materials (microorganisms and bad small components, for example) through simultaneous activity with titanium dioxide in low energy (the visible-ray wavelength range) by the silver phosphate (Ag$_3$PO$_4$).

The inorganic binder may include a polysilicate compound. The polysilicate compound may be composed of colloidal silica (SiO$_2$) and metal alkoxide, for example.

The inorganic binder may include other additional components. The other components may be selected by a person skilled in the art in consideration of a final composition for coating. For example, the inorganic binder may include a stabilizer, an acid catalyst, a hardener, and a metal additive, for example.

The stabilizer may be selected from the group consisting of acetyl acetone, ethyl acetoacetate, iron acetoacetate, alkanolamine, and a combination thereof. The inorganic binder may contain about 0.1 parts to about 0.5 parts by weight of stabilizer.

The acid catalyst may be selected from the group consisting of a phosphate metal catalyst, a nitrate metal catalyst, a phosphate-chloride composite metal catalyst, and a combination thereof. The inorganic binder may contain about 0.01 parts to about 0.5 parts by weight of acid catalyst.

The hardener may be selected from the group consisting of aliphatic polyamine, crylonitrile-modified amine, polyaminde, amido amine, dicyandiamide, amide resin, isocyanate, melamine, and a combination thereof. The inorganic binder may contain about 0.05 parts to about 1 part by weight of hardener.

An aluminum compound may be used as the metal additive. The aluminum compound may be prepared by mixing aluminum isopropoxide with aluminum chloride. The inorganic binder may contain about 0.05 parts to about 0.5 parts by weight of metal additive, for example.

The photocatalyst part 230 may be provided in the form of a solution in which the plurality of composites are mixed with a predetermined solvent. The photocatalyst part 230 may be bonded to the top surface part 223 of the first insulator 220.

For example, the photocatalyst part 230 may be coupled to the top surface part 223 through coating. The coating may include dip coating, spray coating, or screen printing, for example. In a case of the dip coating, a drying temperature may vary according to characteristics of a base material for coating. For example, the dip coating may be performed at a temperature of about 148° C. to about 152° C. for about 9 minutes to about 11 minutes.

As described above, the photocatalyst part 230 may be prepared in the form of the solution and applied to a surface of the first substrate 200. Thus, the photocatalyst part 230 may be easily bonded to the surface of the first substrate 200 (bonding force securement).

When the photocatalyst 230 containing the above-described composites may be disposed on the top surface part 223, water (H$_2$O) or oxygen (O$_2$) may change into reactive oxygen species (ROS) due to the catalyst effect of the photocatalyst 230. The reactive oxygen species may include hydroxy radical (OH$^-$), and hydrogen peroxide (H$_2$O$_2$), for example.

The reactive oxygen species (ROS) may perform strong sterilization (oxidation) and deodorization functions. In detail, reactive oxygen species (ROS) may decompose gas pollutants, such as toluene, and ammonia, for example, as well as biological pollutants, such as bacteria, and molds, for example, which consist of organic materials.

Thus, the photocatalyst part 230 may prevent pollutants generated by air or moisture from being generated, that is, prevent dust from being accumulated or microorganisms from being propagated.

The first substrate 200 may further include the first discharge electrode 240 disposed on the photocatalyst part 230. As described above, the first discharge electrode 240 may be formed by printing the metal oxide paste, for example.

An operation of the first substrate 200 including the above-described components will be briefly described hereinbelow.

When a high voltage which is above a firing voltage is applied to the first discharge electrode 240 including the ground electrode 210 and the pattern frame 243, a discharge phenomenon due to high electric fields may occur around the ground electrode 210 and the first discharge electrode 240. Also, free electrons moving around the ground electrode 210 and the first discharge electrode 240 may be accelerated by the electric fields to collide with neutral molecules (oxygen, and nitrogen, for example) of the air, thereby ionizing the neutral molecules. Thus, a large amount of ions may be generated. The air may be air flowing through the first flow hole 250. The first discharge electrode 240 may be understood as or refer to an "ion generation electrode" that generates Ions.

The second substrate 300 may be disposed to be spaced outward from the first substrate 200. In detail, the second substrate body 301 of the second substrate 300 may include the second discharge electrode 310 that acts with the ground electrode 210 to perform plasma discharge, and the second insulator 320 that surrounds the second discharge electrode 310 to prevent the second discharge electrode 310 from being exposed to the outside. For example, the second ground electrode 310 may be formed of a metal plate, for example, copper (Cu), and the second insulator 320 may be formed of an epoxy resin.

Although separate reference numerals are not given, the second insulator 320 may include a bottom surface part or bottom surface, on which the second ground electrode 310 may be seated, a side surface part or side surface that extends upward from each of both sides of the bottom surface part, and a top surface part or top surface coupled to an upper portion of the side surface part. As the second insulator 320 is similar to the first insulator 220, its detailed description has been omitted. An outside of the second discharge electrode 310 may be completely surrounded by the bottom surface part, the side surface part, and the top surface part of the second insulator 320. Further, a method of manufacturing the second discharge electrode 310 and the second insulator 320 may be the same as the method of manufacturing the ground electrode 210 and the first insulator 220, and thus, repetitive description has been omitted.

Operations of the second substrate 300 and the ground electrode 210 will be briefly described hereinbelow.

When a high voltage which is above the firing voltage is applied to the ground electrode 210 and the second discharge electrode 310, dielectric breakdown between the ground electrode 210 and the second discharge electrode 310 may occur to cause the discharge phenomenon due to the high electric fields, thereby generating a strong plasma region. Also, the free electrons moving through the plasma region may be accelerated by the electric fields to react with the air. As a result, a large amount of OH radicals and ozone may be generated. The air may be air flowing through the second flow hole 350. As the second discharge electrode 310 is spaced apart from the ground electrode 210 by the distance formation part 400, the second discharge electrode 310 may be understood as or refer to a "surface discharge induced electrode" that generates radical ions. As described above, a region A (see FIG. 1) in which the plasma unit 100 is disposed may be defined as a region in which a large amount of OH radicals, ions, and ozone are generated.

Figure 8:
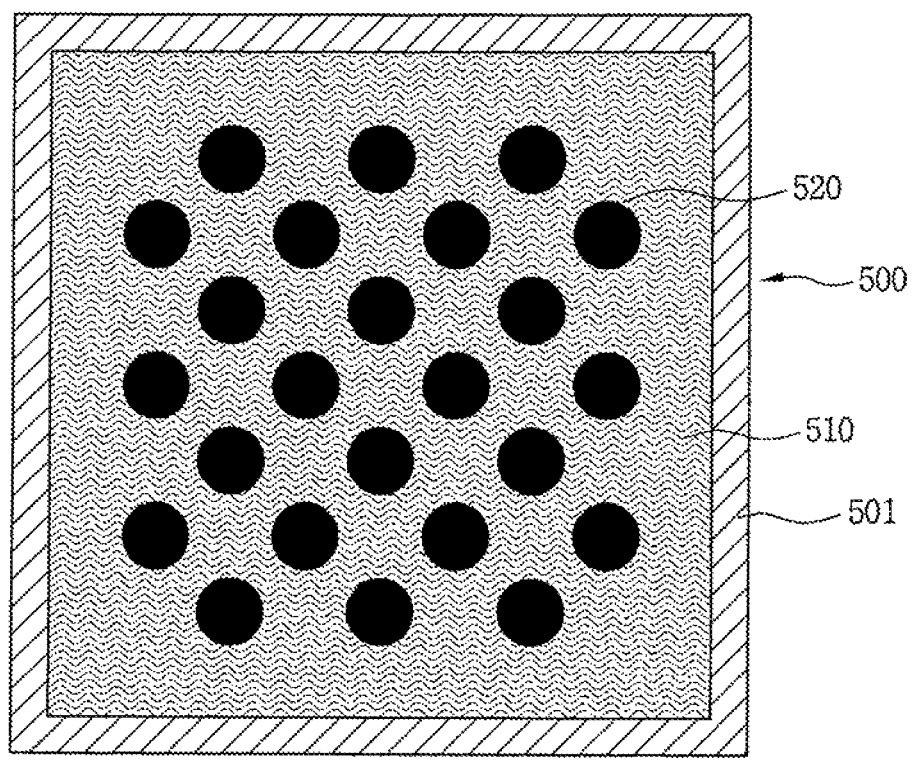
FIG. 8 is a cross-sectional view of a filter unit or filter according to an embodiment.

Hereinafter, the filter unit 500 will be described. FIG. 8 is a cross-sectional view of a filter unit or device according to an embodiment. Referring to FIG. 8, the filter unit or filter 500 according to this embodiment may include a filter frame 510 that defines a body of the filter unit 500, a body part or body 501 that surrounds the filter frame 510 to define an edge of the filter unit 500, and a photocatalyst 520 applied to the filter frame 500 to react with ozone generated from the plasma unit 100.

The filter frame 510 may have a rectangular shape and may be fixed to the frame 600 by the body part 501. The filter frame 500 may have a plurality of through-holes, through which air passing through the plasma unit 100 may pass.

The photocatalyst 520 may be applied to a mesh surface of the filter frame 510. The photocatalyst 520 may receive light to promote chemical reaction. For example, the photocatalyst 520 may be titanium oxide ($TiO_2$). Thus, the photocatalyst 520 may perform a photocatalytic reaction through the light emitted from the light source 610. Also, ions generated by the photocatalyst may flow to the outside through the through-hole. Thus, a region B (see FIG. 1) in which the filter unit 600 is disposed may be defined as a photocatalytic reaction region.

An operation of the sterilization and deodorization apparatus 10 including the above-described components will be briefly described hereinbelow.

Figure 9:
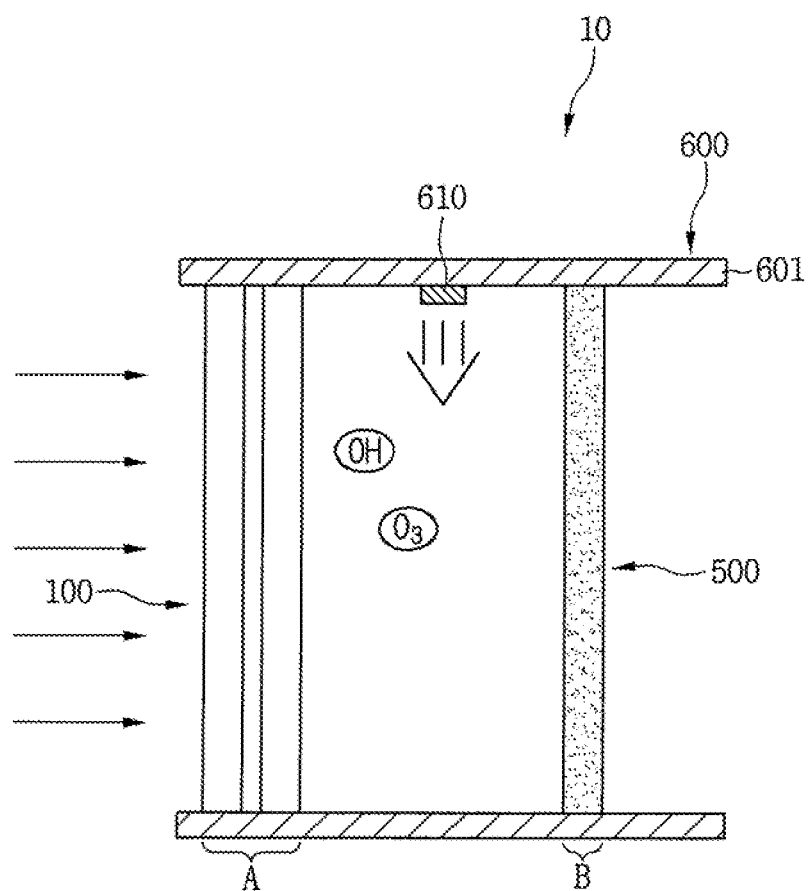
FIG. 9 is a cross-sectional view illustrating an operation of the sterilization and deodorization apparatus of FIG. 1.

FIG. 9 is a cross-sectional view illustrating an operation of the sterilization and deodorization apparatus of FIG. 1. The sterilization and deodorization apparatus 10 may be disposed so that air flows from the region A to the region B in a passage.

A large amount of OH radicals and ozone may be generated in the region A by the plasma unit 100. Also, the ozone ($O_3$) generated in the region A may contact a surface of the photocatalyst 520 to perform a first reaction. The first reaction may be expressed as follows.

That is, OH radicals and oxygen ($O_2$) may be generated by the surface reaction between the ozone and the photocatalyst. The first reaction may be defined or referred to as a surface contact reaction.

Also, in the region B, light emitted from the light source 610 may be irradiated onto the photocatalyst 520 to perform a second reaction on the photocatalyst 520 together with the ozone (Os) generated in the region A. The second reaction may be expressed as follows.

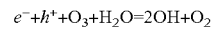

That is, electrons ($e^-$) and holes ($H^+$) which have electric charges may be generated on the surface of the photocatalyst 520 by the light. Then, the electrons ($e^-$) and holes ($H^+$) may react with the ozone ($O_3$) generated in the region A and moisture ($H_2O$) existing in the air to generate OH radicals and oxygen. The second reaction may be defined or referred to as an ozone-photocatalyst reaction.

Thus, according to this embodiment, the reaction of the photocatalyst 520 may improve distribution efficiency using the ozone generated by the plasma unit 100 and the activation reaction of the filter unit 500 when compared to a single reaction of the photocatalyst 520. Also, as ozone generated by the plasma unit 100 is decomposed to generate the OH radicals, air having no ozone may be supplied ultimately.

Figure 10:
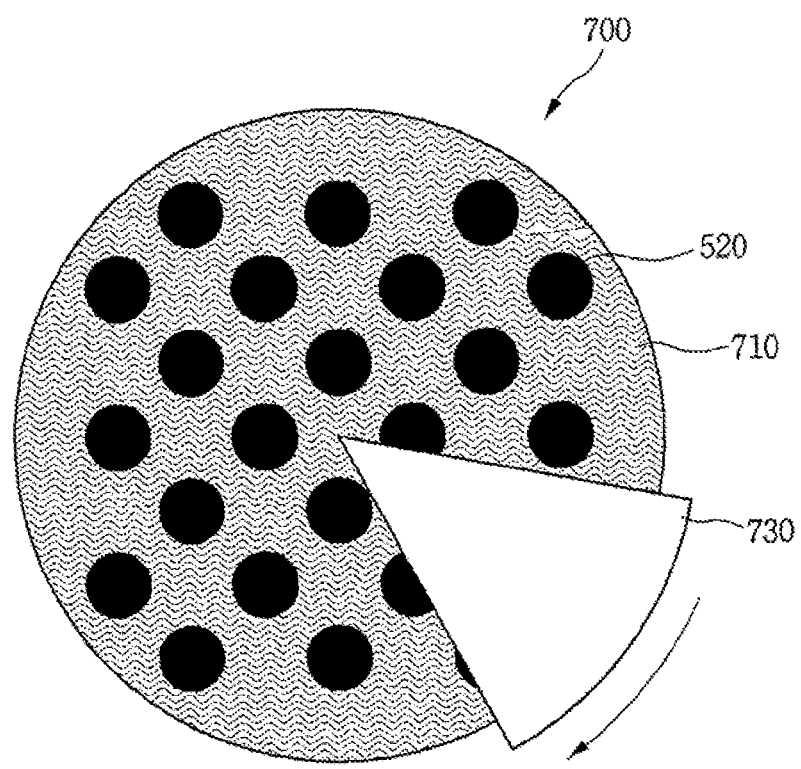
FIG. 10 is a cross-sectional view of a filter unit or filter according to another embodiment.
Figure 11:
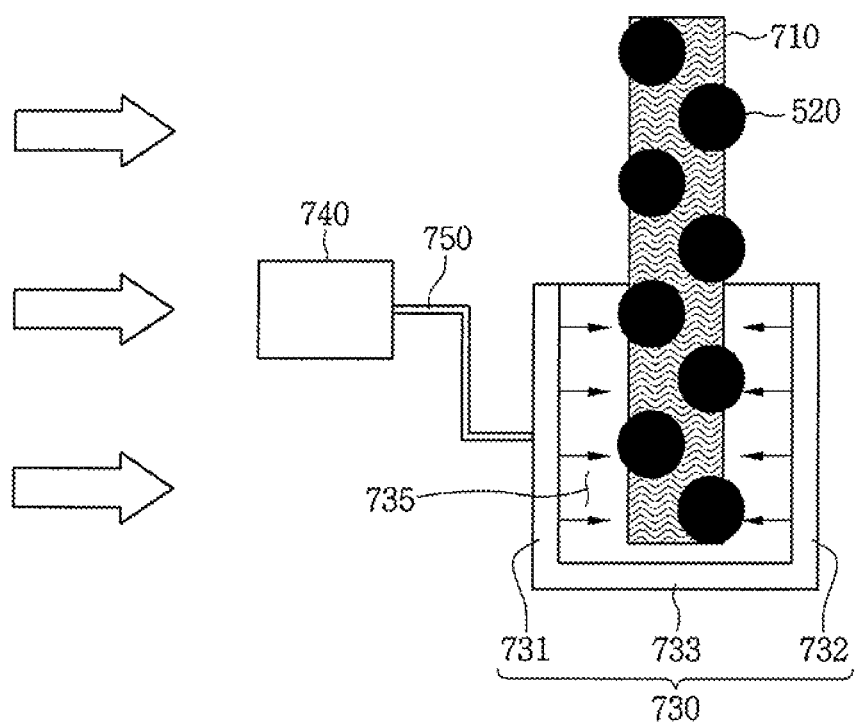
FIG. 11 is a side cross-sectional view of the filter unit of FIG. 10.

FIG. 10 is a cross-sectional view of a filter unit or filter according to another embodiment. FIG. 11 is a side cross-sectional view of the filter unit of FIG. 10. This embodiment may be similar to the previous embodiment except for a filter unit or filter. Thus, only characterized parts of this embodiment will be principally described below, and descriptions of the same parts as that of the previous embodiment will not be repeated.

Referring to FIGS. 10 and 11, a filter unit or filter 700 according to this embodiment may include a filter frame 710 having a plurality of through-holes, photocatalyst 520 applied to the filter frame 710, and a light source part or light source 730 that irradiates light onto at least a portion of the filter frame 710 and coupled to the filter frame 710. In this embodiment, the filter frame 710 may have a circular shape. Further, the plurality of through-holes may be defined in the filter frame 710 having a circular shape so that air may flow therethrough. The photocatalyst 520 may be applied to one surface or both surfaces of the filter frame 710.

Although not shown, a body part or body that surrounds the filter frame 710 may be disposed on or at an edge of the filter frame 710 along the edge of the filter frame 710, like the previous embodiment. Thus, upper and lower ends of the filter frame 710 may be fixed to frame 600.

The light source part 730 may surround at least a portion of both surfaces of the filter frame 710 and be coupled to the filter frame 710 so that the light source part 730 may be rotatable in a clockwise direction or a counterclockwise direction. The light source part 730 may be rotated by coupling a drive motor 740 and a shaft 750 connected to the drive motor 740 to one side of the light source part 730. A rotation rate of the light source part 730 may be controlled by a control unit or controller (not shown).

The light source part 730 may have a fan shape having a predetermined angle. In detail, the light source part 730 may include a first horizontal part or portion 731 that covers at least a portion of one or a first surface of the filter frame 710, a second horizontal part or portion 732 that covers at least a portion of the other or a second surface of the filter frame 710, and a vertical part 733 that connects the first horizontal part 731 to the second horizontal part 732. The first horizontal part 731 and the second horizontal part 732 may have a same shape. That is, each of the first and second horizontal parts 731 and 732 may have a fan shape that covers at least a portion of the filter frame 710 having the circular shape and has a predetermined angle. Also, a portion of the filter frame 710 may be inserted into a groove 735 defined by the first horizontal part 731, the second horizontal part 732, and the vertical part 733.

A light source may be disposed on a surface that faces the filter frame 710 on the first and second horizontal parts 731 and 732. That is, light may be irradiated onto the filter frame 710 inside of the groove 735. Also, the light is not radiated onto a portion of the filter frame 710 that is not accommodated into the groove 735.

Thus, in this embodiment, the light source part 730 may rotate to irradiate light onto only a portion of the filter frame 710, thereby causing a photocatalytic reaction. When the photocatalyst completely reacts with a surface of the filter frame 710 that faces the light source part 710, the light source part 710 may be rotated to irradiate light onto other portions of the filter frame 710, thereby continuously causing the photocatalytic reaction.

Alternatively, the light source part 730 may be fixed, and the filter frame 710 may be rotated to uniformly irradiate light onto the filter frame 710. In this case, a rotational shaft may be connected to a center of the filter frame 710, and the filter frame 710 may be controlled at an adequate rotation rate to rotate in a clockwise direction or a counterclockwise direction.

Figure 12:
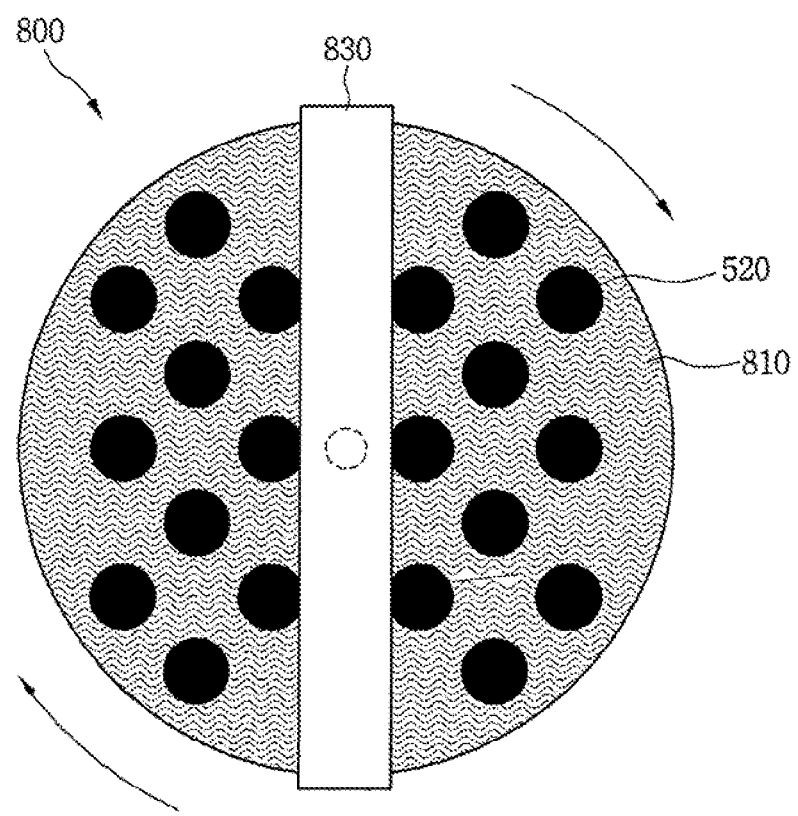
FIG. 12 is a cross-sectional view of a filter unit according to still another embodiment.
Figure 13:
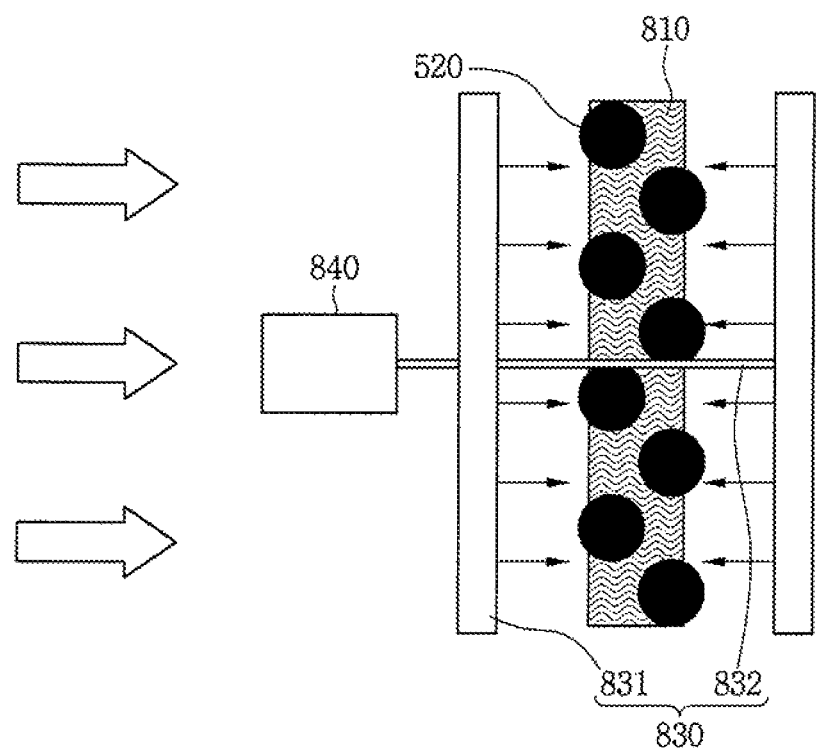
FIG. 13 is a side cross-sectional view of the filter unit of FIG. 12.

FIG. 12 is a cross-sectional view of a filter unit or filter according to still another embodiment. FIG. 13 is a side cross-sectional view of the filter unit of FIG. 12. This embodiment may be similar to the previous embodiments except for a filter unit or filter. Thus, only characterized parts of this embodiment will be principally described below, and descriptions of the same parts as that of the previous embodiments will not be repeated.

Referring to FIGS. 12 and 13, a filter unit or filter 800 according to this embodiment may include a filter frame 810 having a plurality of through-holes, photocatalyst 520 applied to the filter frame 810, and a light source part or light source 830 that irradiates light onto at least a portion of the filter frame 810 and rotatably coupled to the filter frame 810. In this embodiment, the filter frame 810 may have a circular shape. Further, a plurality of through-holes may be defined in the filter frame 810 having a circular shape so that air may flow therethrough. The photocatalyst 520 may be applied to one surface or both surfaces of the filter frame 810.

Although not shown, a body part or body that surrounds the filter frame 810 may be disposed on or at an edge of the filter frame 810 along the edge of the filter frame 810, like the previous embodiment. Thus, upper and lower ends of the filter frame 810 may be fixed to frame 600.

The light source part 830 may include a light irradiation part or portion 831 disposed on each of both surfaces of the filter frame 810, and a rotational shaft 832 that passes through a center of the filter frame 810 to allow the light irradiation part 831 to rotate. The light irradiation part 831 may have a relatively large bar shape having a length greater than a diameter of the filter frame 810. Also, a light source may be disposed on a surface of the light irradiation part 831 that faces the filter frame 810. The rotational shaft 832 may have one side connected to a drive motor 840 to transmit a drive force of the drive motor 840 to the light irradiation part 831.

When light is irradiated from the light irradiation part 831 to the filter frame 810, the photocatalyst 520 applied to the filter frame 810 may react with the light. As the light is not irradiated onto a portion of the filter frame 810 that does not face the light irradiation part 831, the reaction may not occur.

Thus, in this embodiment, the light source part 830 may rotate to irradiate light onto only a portion of the filter frame 810, thereby causing a photocatalytic reaction. When the photocatalyst applied to the surface of the filter frame 810 which is covered by the light irradiation part 831 reacts, the light source part 830 may rotate to continuously irradiate light onto other portions of the filter frame 810, thereby continuously causing the photocatalyst reaction.

Figure 14:
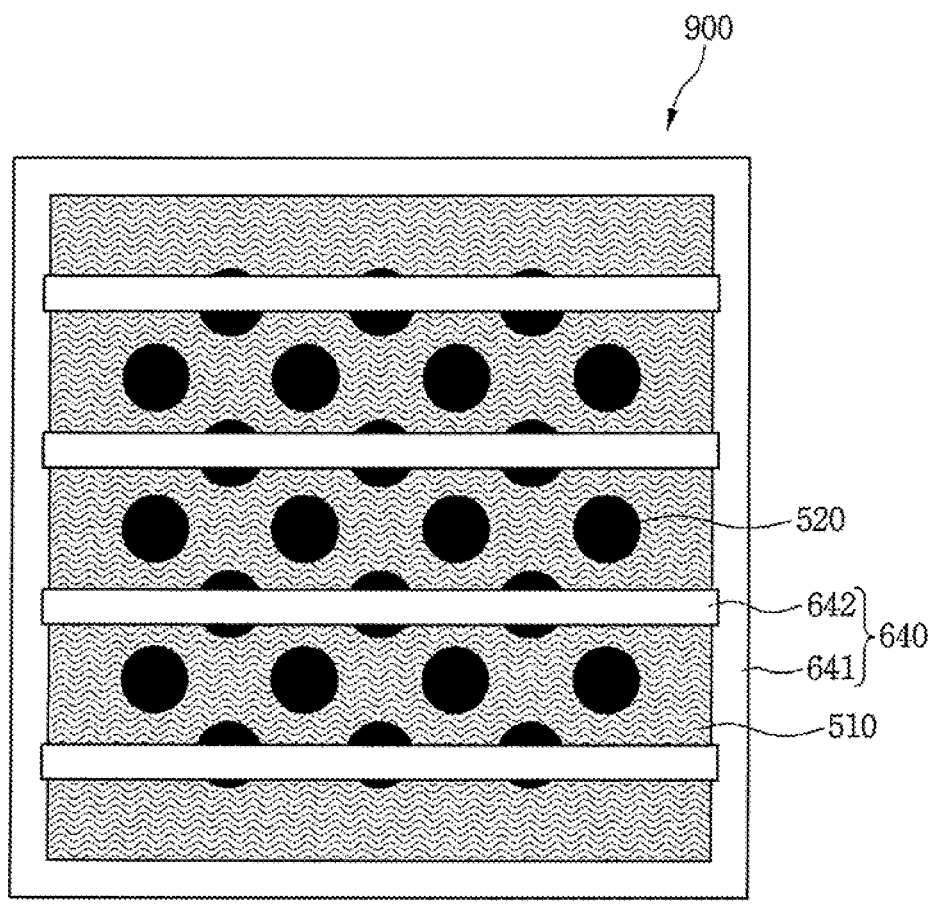
FIG. 14 is a cross-sectional view of a filter unit or fitter according to still another embodiment.
Figure 15:
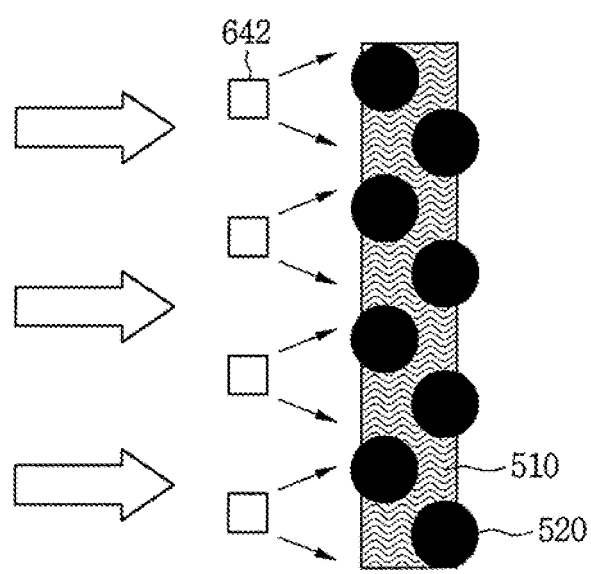
FIG. 15 is a side cross-sectional view of the filter unit of FIG. 14.

FIG. 14 is a cross-sectional view of a filter unit or filter according to still another embodiment. FIG. 15 is a side cross-sectional view of the filter unit of FIG. 14. This embodiment may be similar to the previous embodiments except for a filter unit or filter. Thus, only characterized parts of this embodiment will be principally described below, and descriptions of the same parts as that of the previous embodiments will not be repeated.

Referring to FIGS. 14 and 15, a filter unit or filter 900 according to this embodiment may include fitter frame 510 having a plurality of through-holes, photocatalyst 520 applied to the filter frame 510, and a light source part or light source 640 disposed to be spaced apart from the filter frame 510 to irradiate light to the filter frame 510. The light source part 640 may include a light source frame 641 that defines an outer frame, and a plurality of light sources 642 disposed on the light source frame 641 in a line. Referring to FIG. 14, four light sources 642 may be horizontally disposed on the light source frame 641, as shown in FIG. 14; however, embodiments are not limited thereto.

Each of the plurality of light sources 642 may irradiate light to the filter frame 510. Thus, the photocatalyst 520 applied to the filter frame 510 may react with the light.

Thus, according to this embodiment, as the plurality of light sources 642 may be disposed at a predetermined distance on the light source frame 641, the light may be uniformly irradiated onto an entire surface of the filter frame 510 to quickly perform the photocatalytic reaction.

The sterilization and deodorization apparatus according to embodiments disclosed herein may have at least the following advantages.

First, as ozone generated from the plasma unit is converted into the OH radicals through or by the photocatalyst, an amount of ozone may be reduced. Thus, bad smells and pollutants may be efficiently removed.

Second, as light is irradiated onto the photocatalyst applied to the filter frame using the rotatably coupled light source, a continuous photocatalyst reaction may be realized.

Third, as the light in the visible light region is used, the filter may be easily recycled, and also the product may be easily designed.

Embodiments disclosed herein provide a sterilization and deodorization apparatus that is capable of removing pollutants.

Embodiments disclosed herein provide a sterilization and deodorization apparatus that may include a frame that defines an outer appearance; a plasma unit or device disposed on or at one or a first side of the frame, the plasma unit forming a plasma region to generate a plurality of ions; and a filter unit or filter disposed on or at the other or a second side of the frame which is spaced apart from the frame unit. The filter unit may include a filter frame having a plurality of through-holes so that air may pass therethrough; and a photocatalyst applied to the filter frame to perform photocatalytic reaction. The sterilization and deodorization apparatus may further include a light source disposed on or at one side of the frame to irradiate light onto the filter unit. The light irradiated from the light source may have a wavelength of visible light region.

The air may flow from the plasma unit to the filter unit. The plurality of ions may include ozone ($O_3$), and the photocatalyst may include titanium oxide ($TiO_2$).

The sterilization and deodorization apparatus may further include a light source part or light source rotatably coupled to the filter frame, that irradiates light onto at least a portion of the filter frame. The light source part may include a first horizontal part or portion that covers a portion of one or a first surface of the filter frame; a second horizontal part or portion having a same shape as the first horizontal part, the second horizontal part covering a portion of the other or a second surface of the filter frame; and a vertical part that connects the first horizontal part to the second horizontal part, and a light source that irradiates light onto the filter frame disposed on each of the first and second horizontal parts. The sterilization and deodorization apparatus may further include a drive motor disposed on or at one side of the light source part to rotate the light source part.

The sterilization and deodorization apparatus may further include a light source part or portion that covers at least a portion of the filter frame. The at least a portion of the filter frame may be covered by the light source part to rotate. The light source part may include a first horizontal part or portion that covers a portion of one or a first surface of the filter frame; a second horizontal part or portion having a same shape as the first horizontal part, the second horizontal part covering a portion of the other or a second surface of the filter frame; a vertical part that connects the first horizontal part to the second horizontal part; and a light source that irradiates light onto the filter frame disposed on each of the first and second horizontal parts.

The sterilization and deodorization apparatus may further include a light source part or light source disposed to be spaced apart from the filter frame to irradiate light onto the filter frame. The light source part may include a light source frame that defines an outer frame; and a plurality of light sources disposed on the light source frame in a line to irradiate light onto the filter frame.

The plasma unit may include first and second substrates, which may be disposed opposite to each other, and a distance formation part that spaces the first and second substrates from each other disposed between the first and second substrates. The first substrate may include a first substrate body having a plate shape; at least one first flow hole that passes through the first substrate body to guide a flow of air; and a pattern frame disposed to surround at least a portion of the first flow hole. The second substrate may include a second substrate body having a plate shape; and at least one second flow hole that passes through the second substrate body to guide a flow of air. The pattern frame may include a closed pattern that surrounds the first flow hole; and a discharge tip that protrudes from an outer circumferential surface of the pattern. The photocatalyst may be applied to a mesh surface of the filter frame, which may be formed by the plurality of through-holes.

Embodiments disclosed herein further provide a sterilization and deodorization apparatus that may include a frame in which air flows; a plasma unit or device disposed inside of the frame, the plasma unit forming a plasma region to generate a plurality of ions; a filter unit or filter disposed to be spaced apart from the plasma unit inside of the frame, the filter unit including a filter frame to which a photocatalyst that performs a photocatalytic reaction may be applied; and a light source disposed between the plasma unit and the filter unit inside of the frame to irradiate light onto the filter unit. The light irradiated from the light source may have a wavelength of a visible light region.

The air may flow from the plasma unit to the filter unit. The plurality of ions may include ozone ($O_3$), and the photocatalyst may include titanium oxide ($TiO_2$).

The filter frame may have a plurality of through-holes so that the air may pass therethrough. The photocatalyst may be applied to a mesh surface of the filter frame, which may be formed by the plurality of through-holes.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:
1. A sterilization and deodorization apparatus, comprising:
   a frame that defines an outer appearance of the sterilization and deodorization apparatus;
   a plasma device disposed at a first side of the frame, that forms a plasma region to generate a plurality of ions; and
   a filter disposed at a second side of the frame and spaced apart from the plasma device, wherein the filter includes:
      a filter frame having a plurality of through-holes that passes air therethrough; and
      a photocatalyst applied to the filter frame to perform a photocatalytic reaction, wherein the plasma device includes first and second substrates, which are disposed opposite to each other, wherein a predetermined space is provided between the first and second substrates, wherein the first substrate includes:
      a first substrate body having a plate shape;
      at least one first flow hole that passes through the first substrate body to guide a flow of air; and
      at least one pattern frame disposed to surround at least a portion of the at least one first flow hole, and wherein the first substrate body includes:

a ground electrode;

a first insulator that surrounds the ground electrode; and a photocatalyst portion disposed on at least one surface of the first insulator.

2. The sterilization and deodorization apparatus according to claim 1, further including a light source disposed at one side of the frame to irradiate light onto the filter.

3. The sterilization and deodorization apparatus according to claim 2, wherein the light irradiated from the light source has a wavelength of a visible light region.

4. The sterilization and deodorization apparatus according to claim 1, wherein the air flows from the plasma device to the filter.

5. The sterilization and deodorization apparatus according to claim 1, wherein the plurality of ions includes ozone ($O_3$), and wherein the photocatalyst includes titanium oxide ($TiO_2$).

6. The sterilization and deodorization apparatus according to claim 1, further including a light source assembly rotatably coupled to the filter frame, that irradiates light onto at least a portion of the filter frame.

7. The sterilization and deodorization apparatus according to claim 6, wherein the light source assembly includes:

a first horizontal portion that covers a portion of a first surface of the filter frame;

a second horizontal portion having a same shape as the first horizontal portion, wherein the second horizontal portion covers a portion of a second surface of the filter frame;

a vertical portion that connects the first horizontal portion to the second horizontal portion; and a light source that irradiates light onto the filter frame disposed on each of the first and second horizontal portions.

8. The sterilization and deodorization apparatus according to claim 6, further including a drive motor disposed at one side of the light source assembly to rotate the light source assembly.

9. The sterilization and deodorization apparatus according to claim 1, further including a light source assembly that covers at least a portion of the filter frame.

10. The sterilization and deodorization apparatus according to claim 9, wherein the light source assembly includes:

a first horizontal portion that covers a portion of a first surface of the filter frame;

a second horizontal portion having a same shape as the first horizontal portion, wherein the second horizontal portion covers a portion of a second surface of the filter frame;

a vertical portion that connects the first horizontal portion to the second horizontal portion; and a light source that irradiates light onto the filter frame disposed on each of the first and second horizontal portions.

11. The sterilization and deodorization apparatus according to claim 1, further including a light source assembly disposed to be spaced apart from the filter frame to irradiate light onto the filter frame, wherein the light source assembly includes:

a light source frame that defines an outer frame of the light source assembly; and a plurality of light sources disposed on the light source frame in a line to irradiate light onto the filter frame.

12. The sterilization and deodorization apparatus according to claim 1, wherein the second substrate includes:

a second substrate body having a plate shape; and at least one second flow hole that passes through the second substrate body to guide the flow of the air.

13. The sterilization and deodorization apparatus according to claim 12, wherein the second substrate body includes:

a second discharge electrode; and a second insulator that surrounds the second discharge electrode.

14. The sterilization and deodorization apparatus according to claim 12, wherein the at least one first flow hole communicates with the at least one second flow hole.

15. The sterilization and deodorization apparatus according to claim 1, wherein the at least one pattern frame includes:

a closed pattern that surrounds the at least one first flow hole; and at least one discharge tip that protrudes from an outer circumferential surface of the closed pattern.

16. The sterilization and deodorization apparatus according to claim 1, wherein the photocatalyst is applied to a mesh surface of the filter frame, which is formed by the plurality of through-holes.

17. The sterilization and deodorization apparatus according to claim 1, wherein the photocatalyst reduces ozone, which is produced by the plasma device.

18. The sterilization and deodorization apparatus according to claim 1, wherein the first substrate further includes:

a discharge electrode portion; and a connection line that extends from the discharge electrode portion and connects the discharge electrode portion with the at least one pattern frame.

19. The sterilization and deodorization apparatus according to claim 18, wherein the at least one pattern frame, the discharge electrode portion, and the connection line form a first discharge electrode, and wherein the first discharge electrode is disposed on a surface of the first substrate body.

20. The sterilization and deodorization apparatus according to claim 1, wherein the at least one first flow hole includes a plurality of first flow holes, and wherein the at least one pattern frame includes a plurality of pattern frames.

* * * * *